United States Patent [19]

Omagari

[11] Patent Number: 4,621,618

[45] Date of Patent: Nov. 11, 1986

[54] DUAL VIEWING AND CONTROL APPARATUS FOR ENDOSCOPE

[75] Inventor: Yasuhiko Omagari, Hachioji, Japan

[73] Assignee: Olympus Optical Company, Ltd., Japan

[21] Appl. No.: 706,121

[22] Filed: Feb. 27, 1985

[30] Foreign Application Priority Data

Feb. 28, 1984 [JP] Japan .................................. 59-36722

[51] Int. Cl.⁴ ............................ A61B 1/02; A61B 1/06
[52] U.S. Cl. ............................................ 128/6; 358/98
[58] Field of Search ........................... 128/3, 4, 5, 6, 7; 358/98

[56] References Cited

U.S. PATENT DOCUMENTS

| | | | |
|---|---|---|---|
| 1,551,770 | 9/1925 | Palmeter | 128/6 |
| 4,102,333 | 7/1978 | Storz | 128/6 |
| 4,283,115 | 8/1981 | Fraissl | 128/4 X |
| 4,517,963 | 5/1985 | Michel | 128/6 |
| 4,552,131 | 11/1985 | Omagari | 128/6 |

FOREIGN PATENT DOCUMENTS 0029556  6/1981  European Pat. Off. .
0079525  5/1983  European Pat. Off. .

Primary Examiner—William H. Grieb
Attorney, Agent, or Firm—Ostrolenk, Faber, Gerb & Soffen

[57] ABSTRACT

An endoscope apparatus includes an endoscope of the motor drive type which includes at least an image pickup means within an insertable portion thereof and are operable by giving operating orders to drive units for bending, air and water feed operations. The endoscope apparatus further includes observation means and operating means for the bending, air and water feed which are disposed respectively at positions remote from the endoscope body in such a manner that a plurality of operators of the endoscope can simultaneously perform the same operations while observing the same image being observed.

27 Claims, 7 Drawing Figures

```
Dr:
Date:            No:
Name:
Age:             Sex:                    85
Address:
Telephone:

Medication:      Past Hx:
Sympton:         Family Hx:

Biopsy:
Polypectomy:

Level of Insertion:
Scop Model:

X-Ray Diagnosis:

Clinical Diagnosis:

Follow-Up Date:
```

FIG. 7

DUAL VIEWING AND CONTROL APPARATUS FOR ENDOSCOPE

BACKGROUND OF THE INVENTION

The present invention relates to an endoscope apparatus, and more particularly, to means for operating an endoscope apparatus.

In general, an endoscope should exhibit the following characteristics: it should have a bendable insertion portion, it should be capable of feeding air and water to the coelom and it should be capable of suctioning coeliac fluid. These functions are effected manually and/or electrically by operating control members such as knobs and/or buttons provided on an operating portion of the endoscope located at the proximal end thereof. In presently used mechanisms for operating endoscopes, the control members are provided on the operating portion of the endoscope in a concentrated manner. The concentrated arrangement of the operating members, however, has many disadvantages.

By way of example, when two observers, one an instructor such as a physician and the other a person to be instructed such as an intern, observe a display scope mounted on the endoscope with the physician standing on the operator side (the holder side) of the endoscope and the intern standing on the display side of the endoscope, the intern cannot easily relate the instruction he is being given to the control operations of the endoscope because he is unable to operate the endoscope from the instructed side of the endoscope. When the intern stands on the operator side and the physician stands on the display side, the physician cannot observe the intern's operation of the control knobs and therefore the intern always has some apprehensions that he will operate the endoscope improperly. In either case, the instruction does not go smoothly.

Some endoscopes have an arrangement in which a plurality of persons can simultaneously observe an image to be observed by mounting a television set on an eyepiece portion of the endoscope. In this case, since the operating portion and its associated elements are heavy, they are conventionally suspended from the ceiling, resulting in difficulty in operation.

SUMMARY OF THE INVENTION

It is an object of the present invention, in view of the foregoing, to provide an endoscope apparatus which is operable at any desired position of the apparatus by utilizing an endoscope of the motor drive type.

According to the present invention, the endoscope is operable not only at the endoscope body but also at any position remote from the endoscope body. As a result, the endoscope is adapted to be operable under optimum conditions and thus it is possible to solve the conventional disadvantages.

DESCRIPTION OF PREFERRED EMBODIMENTS

Figure 1:
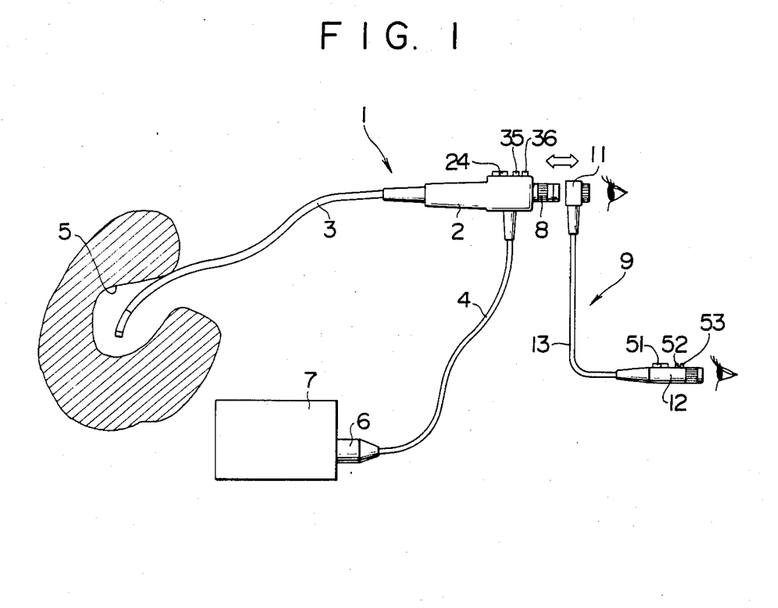
FIG. 1 is a schematic diagram of an endoscope apparatus which is in use according to a first embodiment of the present invention.

Referring now to FIG. 1, which illustrates a first embodiment of the present invention, an endoscope which comprises an operating body 2 and an elongated insertable portion 3, and a universal cord 4 for guiding light which are connected to the operating body 2. The insertable portion 3 is to be insertable into the coeliac cavity 5, for example. A connector 6 is provided on the tip end of the cord 4 to be connected to a light source unit 7. A variety of operating switches 24, 35, 36 which will be described later and an eyepiece portion 8 are provided on the operating body 2. A display device 9 and/or a display scope (not shown) is detachably mounted on the eyepiece portion 8. The display device 9 comprises a parent eyepiece portion 11 and a child eyepiece portion 12, both of them are coupled through an elongated flexible tube 13 to each other.

The endoscope 1, the light source unit 7 and the display device 9 will be described in detail with a reference to FIG. 2. The insertable portion 3 includes a distal portion 16 which is coupled through a bendable tube portion 15 to the tip end of a flexible tube portion 14. Plural pairs of bending operation wires 17, 17' are introduced into the insertable portion 3. The tip ends of the wires 17, 17' are connected to the distal portion 16 of the insertable portion 3. The proximal ends of the wires 17, 17' are fixed to a drum 18 which is disposed within the operating body 2, in such a manner that each pair of wires 17, 17', are arranged in a symmetrical manner with respect to the center of the drum 18 and the pairs are arranged in different positions on the periphery of the drum 18. A worm wheel 19 is coaxially attached to the drum 18, which wheel engages a worm 22 mounted on a drive shaft of a motor 21. The start, stop and rotational direction of the motor 21 is controlled by operating a switch 24 for the bending operation which is disposed on an operating board 23 formed on the operating body 2.

A tube 25 for air and water feed is arranged within the insertable portion 3. The distal end of the tube 25 is connected to a nozzle 26 of the distal portion 16 and the proximal end thereof is connected to an air feed tube 27 and a water feed tube 28. The tubes 27, 28 are connected through the inside of the operating body 2 and the cord 4 and further through the connector 6 to an air pump 29 and a water pump 31 within the light source unit 7, respectively. First and second electromagnetic valves 32, 33 are disposed in portions of the air and water feed tubes 27, 28, respectively, which portions pass through the operating body 2, to automatically open and close the air and water feed tubes 27, 28. Air and water feed switches 35, 36 are provided on the operating board 23 to close and open the respective first and second electromagnetic valves 32, 33. Specifically, the first electromagnetic valve 32 is opened by pressing the air feed switch 35 and the second electromagnetic valve 33 is opened by pressing the water feed switch 36. The switches 35, 36 are electrically connected to the air and water feed pumps 29, 31, respectively, to activate the air and water pumps 29, 31 in response to the openings of the first and second electromagnetic valves 32, 33.

A light guide 37 is disposed within the insertable portion 3, operating body 2 and universal cord 4 so as to extend therethrough. The light guide 37 has its distal end connected to an illumination window 38 in the distal portion 16 and its proximal end connected to a light guide tube 39 provided in the connector 6. The light guide tube 39 receives illumination light from a light source 41 within the light source unit 7 to transmit the illumination light to the light guide 37.

An image guide 42 is disposed within the insertable portion 3 and the operating body 2 so as to extend therethrough. The image guide 42 has its distal end 16 connected to an objective lens 43 for the purpose of observation disposed in the distal portion 16 and its proximal end optically connected to an eyepiece lens 8a provided in the eyepiece portion 8.

The parent eyepiece portion 11 in the display device 9 is detachably mounted on the eyepiece portion 8 of the endoscope 1. A partially reflecting prism 44 is disposed as an optically splitting means in opposing relationship with the eyepiece lens 8a within the parent eyepiece portion 11 so that part of light transmitted from the eyepiece portion 8 is reflected toward the side direction thereof and the remaining light is transmitted therethrough. The transmitted light is fed to a parent eyepiece lens 45 provided adjacent the prism 44 so as to be observed at the parent eyepiece portion 11. The light reflected toward the side direction by the prism 44 forms an image on one end plane of an image guide 47 for the display purpose through an image forming lens 46. The image guide 47 is led through the flexible tube 13 to the child eyepiece portion 12 to be optically connected to a child eyepiece lens 48 provided in the child eyepiece portion 12.

A variety of switches are provided on the child eyepiece portion 12, including a second switch 51 for the bending operation, a second switch 52 for the air feed and a second switch 53 for the water feed. These switches 51, 52, 53 are operating members and serve the purpose as the switches 24, 35, 36. With the second set of switches 51, 52, 53 on the child eyepiece portion it is possible to perform the same operations as those performed by the first set of switches 24, 35, 36 on the operating body 2 of the endoscope 1 side. The second set of switches 51, 52, 53 are electrically connected to the first set of switches 24, 35, 36. Specifically, two sets of contacts 54, 54' and 55, 55' are provided on the upper surface of the eyepiece portion 8 and the lower surface of the parent eyepiece portion 11, respectively, such that both of the eyepiece portions 8, 11 are brought into electrical contact with each other. The contacts 54, 54' in the endoscope 1 are connected to the switches 24, 35, 36, and the contacts 55, 55' in the display device 9 are connected to the switches 51, 52, 53 such that when the display device 9 is mounted on the endoscope 1, both of the contact sets 54, 54' and 55, 55' are automatically brought into contact with each other so as to be electrically connected.

In operation, when the display device 9 is not mounted on the endoscope 1, it is possible to perform normal observation through the eyepiece portion 8 and also to bend the bending tube portion 15 and to perform the air feed and water feed operations by operating the switches 24, 35, 36 which are the first operating members on the operating body 2. Specifically, when the switch 24 for the bending operation is pressed the motor 21 is activated to rotate the drum 18 through the worm 22 and the worm wheel 19, with the result that the bendable tube portion 15 is bent in a direction where a pair of wires 17, 17' are pulled and pushed. The bending direction is defined by selecting the switch 24 for the bending operation so as to determine a direction of rotation of the motor 21. When the air feed switch 35 is operated, the first electromagnetic valve 32 is opened to feed air from the pump 29 through the air feed tubes 27, 25 to the nozzle 26. When the water feed switch 36 is operated, the second electromagnetic valve 33 is opened to feed water from the pump 31 through the tubes 28, 25 to the nozzle 26.

Figure 2:
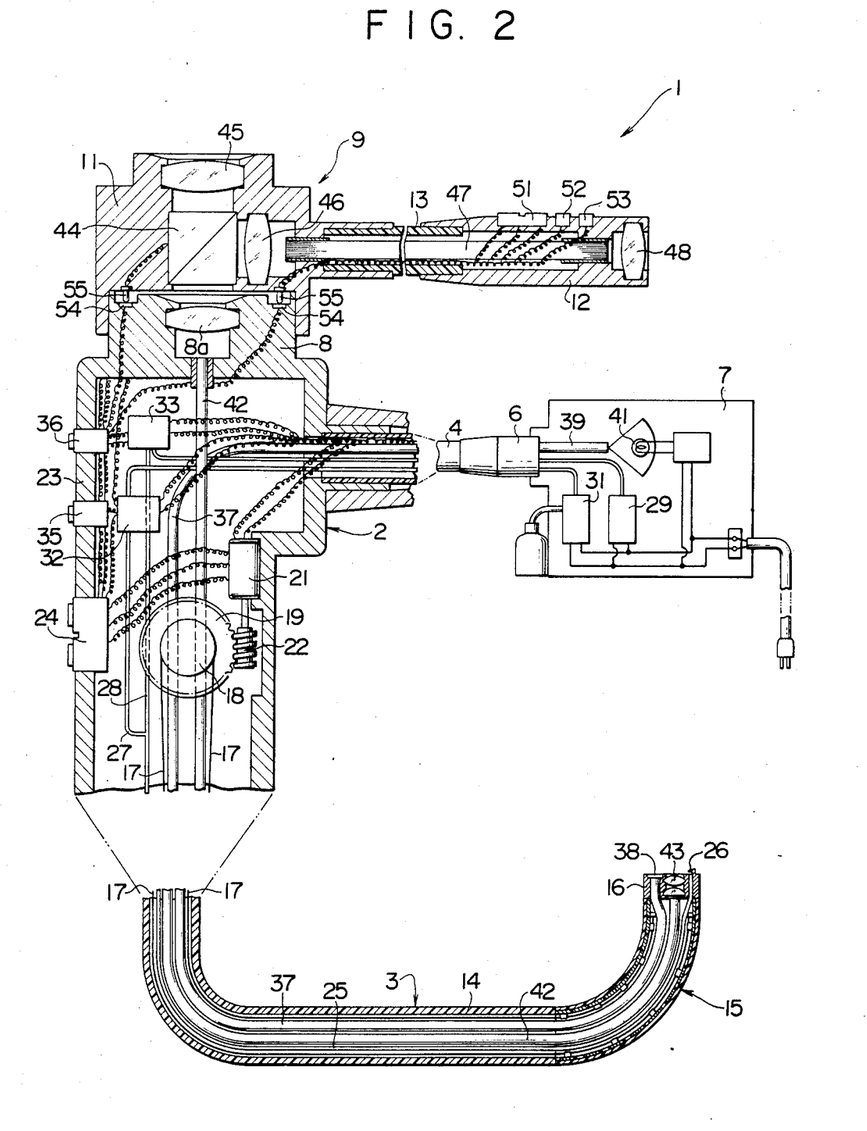
FIG. 2 is an enlarged sectional view of the essential parts of the endoscope apparatus shown in FIG. 1.

When the display device 9 is mounted on the endoscope 1, as shown in FIG. 2, it is possible to perform the observation operation by way of each of the parent eyepiece portion 11 and the child eyepiece portion 12. It is also possible to perform the same bending, air feed and liquid feed operations as those stated above by employing second switches 51, 52, 53 which are the second operating members in addition to the first operating members. Specifically, it is possible to perform these operations not only at the operating body 2 by a first person looking through the parent eyepiece portion 11 with the first operating members but also at the child eyepiece portion 12 by a second person looking through the child eyepiece portion 12 with the second operating members. It will be understood that a priority switch (not shown) may be provided which sets a person to have priority when operated simultaneously by the first and second persons so that either of them can preferentially operate the endoscope 1.

Figure 3:
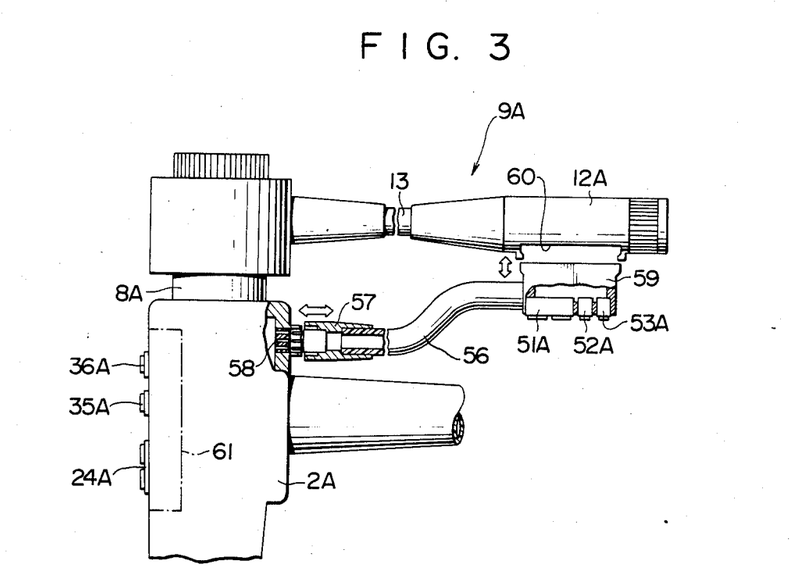
FIG. 3 is enlarged, partially cutaway side view of an endoscope apparatus according to a second embodiment of the present invention.

Referring to FIG. 3, which illustrates a second embodiment of the present invention, a second switch 51A for the bending operation, a second air feed switch 52A and a second water feed switch 53A are provided on a child eyepiece portion 12A of a display device 9A and are attached to a switch block 59 which is detachably mounted on a holder 60 provided on the child eyepiece portion 12A. The switch block 59 is connected to one end of a cable 56, for transmitting a signal. A connector 57 is provided at the other end of the cable 56 which connector includes electrical contacts connected through the cable 56 to corresponding switches 51A, 52A, 53A. The connector 57 is detachably mounted on a connector mount 58 provided on an operating body 2A of the endoscope. The connector 57 has electrical contacts connected to corresponding electrical contacts of the mount 58 when mounted thereon. The contacts of the mount 58 are also connected to various operating mechanisms and a light source unit within the operating body 2A in a manner similar to the first embodiment mentioned above. The apparatus of the second embodiment is used by mounting the connector 57 on the mount 58 and the switch block 59 on the holder 60 after the display device 9A is fixed to the apparatus.

It will be understood that when switch block 59 is used by disconnecting it from the child eyepiece portion 12A, both the switch block 59 and the eyepiece portion 12A may be used by separately taking in observer's right and left hands.

In the apparatus of the second embodiment, first operating members comprising a switch 24A for the bending operation, an air feed switch 35A and a water feed switch 36A are built in a switch block 61 which is detachably attached to the operating body 2A. When the switch block 61 is disconnected from the operating body 2A, the endoscope 1 side can be coupled to a cable and a transmitting means such as for ultrasonic waves, infrared rays, electric waves and the like.

It should be understood that in th first and second embodiments, suction tubes for aspirating air, water, coeliac fluid and the like into the insertable portion, electromagnetic valves for closing and opening the suction tubes, suction switches for controlling the electromagnetic valves, and suction pumps may be provided so as to permit the foregoing operations to be performed.

Figure 4:
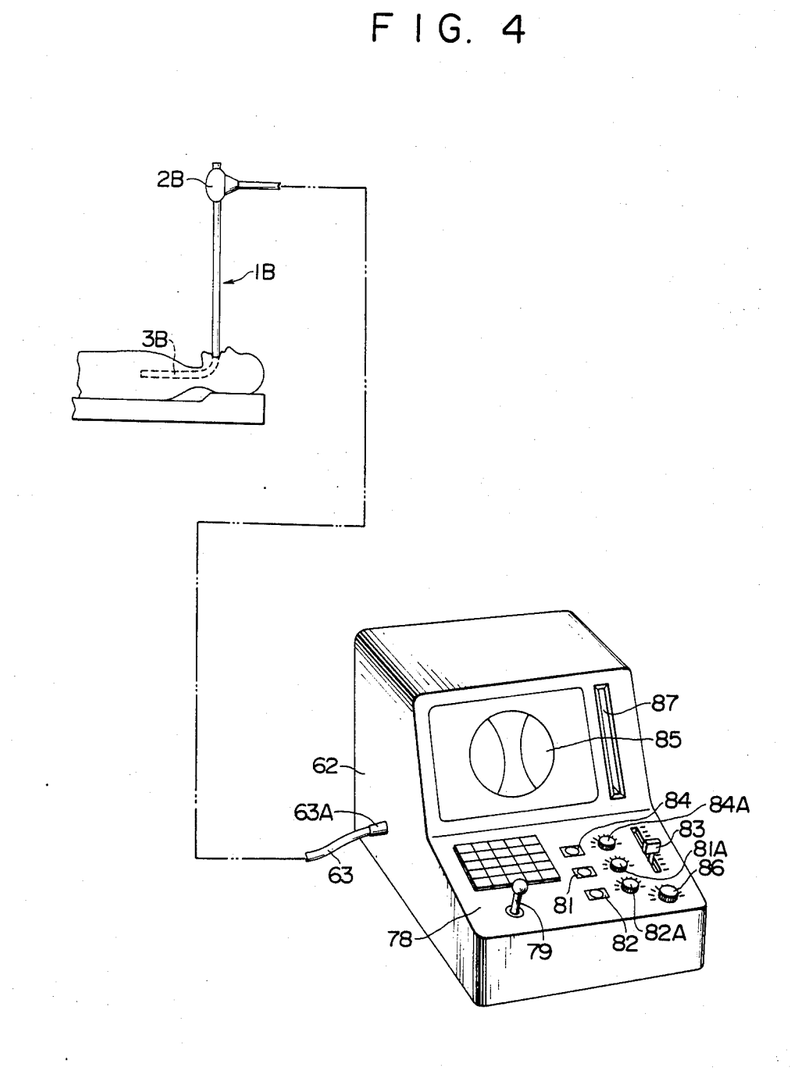
FIG. 4 is a schematic diagram of an endoscope apparatus which is in use according to a third embodiment of the present invention.
Figure 5:
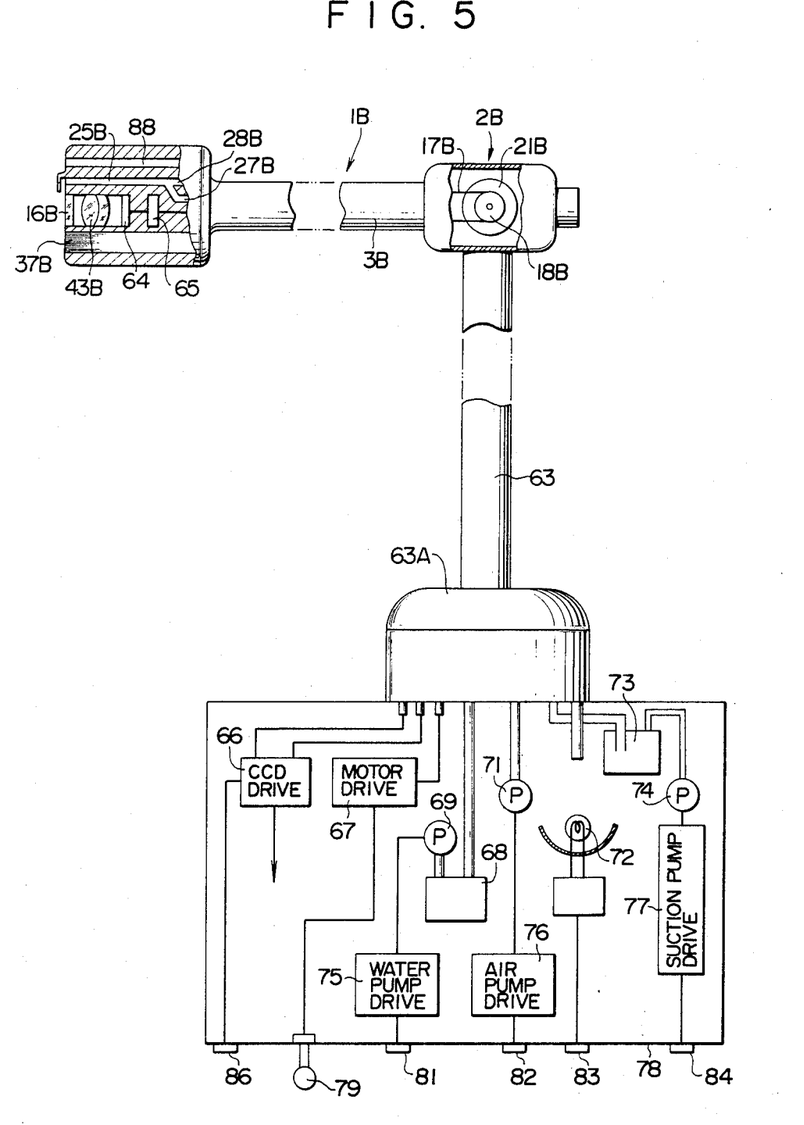
FIG. 5 is a schematic diagram of the essential parts of the endoscope apparatus shown in FIG. 4.

Referring to FIGS. 4 and 5, which illustrate a third embodiment of the present invention, an endoscope 1B, is operated using a centralized control apparatus 62, making operating members on the endoscope body thereof unnecessary. The control apparatus 62 comprises a control desk 78 and a television set 85. A connecting cable 63 is removably connected to the control apparatus 62 by a connector 63A. The endoscope 1B comprises an insertable portion 3B and a drive body 2B. A light guide 37B. a tube 25B, an air feed tube 27B, a water feed tube 28B, a suction tube 88 and the like are arranged within the insertable portion 3B. A motor 21B, a bending operating wire 17B, a drum 18B and the like are disposed within the drive body 2B. The endoscope 1B is particularly provided with an image pickup element 64 comprising a CCD (charge coupled device) and an amplifier 65 for the image pickup element at the distal end portion 16B of the insertable portion 3B in opposing relationship with an objective lens 43B, as shown in FIG. 5, to which cables for driving the CCD and for signals are connected. The control apparatus 62 includes a CCD drive circuit 66 to which the CCD drive cable and the signal cable are connected, a motor drive circuit 67 to which a motor drive cable is connected, a water tank 68 to which the water feed tube 28B and a water tank 68 to which the water feed tube 28B and a water feed pump 69 are connected, an air feed pump 71 to which the air feed tube 27B is connected, a light source 72, a suction tank 73, a suction pump 74, a drive circuit 75 for the water feed pump 69, a drive circuit 76 for the air feed pump 71 and a drive circuit 77 for the suction pump 74. The control desk 78 is provided with operating members for operating the endoscope 1B. Specifically, the control desk 78 has a joy stick 79 to which the motor drive circuit 67 is connected, a water feed button 81 to which the drive circuit 75 is connected, an air feed button 82 to which the drive circuit 76 is connected, a light intensity adjusting button 83 to which the light source 72 is connected, a suction button 84 to which the drive circuit 77 is connected, a button 86 for adjusting color sensitivity of the television set 85, buttons 82A, 81A, 84A for respectively adjusting air feed, water feed and suction pressures and a recording unit 87 such as a magnetic disc recorded for recording data of patients and picture images.

Figure 7:
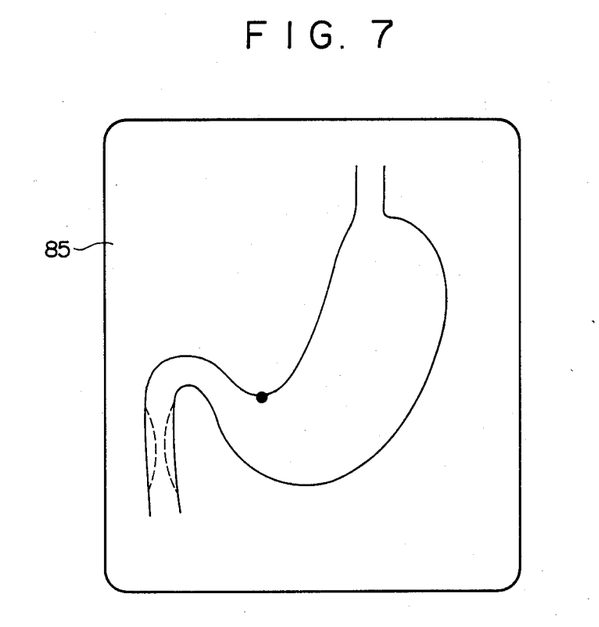

With the arrangement of the third embodiment, it is possible to remotely operate the endoscope 1B by operating the above stated various operating members concentratedly arranged on the control desk 78 and even while being seated thereat. It is further possible to simultaneously perform the observation and operations by a plurality of operators. In addition, when a typical picture of the stomach and the like is reproduced on the television set 85, it is possible for an instructor to indicate a presently observing region with a light pen to a person being instructed so that precise instructions can be simply given. When a position of an affected part is located, it can be entered into the typical picture of the stomach by indicating it with a light pen as shown by FIG. 7, and it is then possible to record it on a magnetic disc and the like as case history information.

Figure 6:
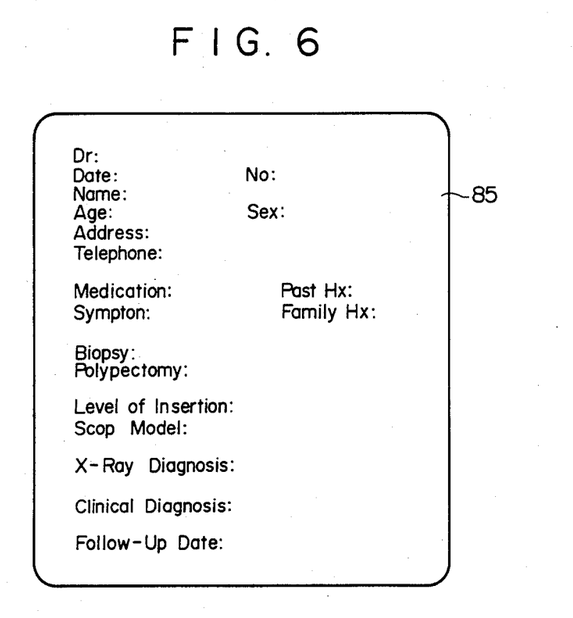
FIGS. 6 and 7 are views of pictures on a television set of the endoscope apparatus shown in FIG. 4.

It is to be noted that the endoscope 1B is held by a paramedic, for example. Both the endoscope 1B and the light source 72 can be operated at the same position, thus facilitating the operations. In addition, it is possible to input case history information as shown in FIG. 6 by operations on the control desk 78.

The present invention is not limited to functions of the foregoing embodiments and may provide other functions of an endoscope such as forceps raising and four directional bending by providing operating members such as switches.

I claim:

1. A dual viewing and control endoscope apparatus comprising:
   an endoscope, including an operating body, an endoscope eyepiece located on said operating body, an insertable portion extending from said operating body, an image pickup means for transmitting an optical image from a distal end of said insertable portion to said endoscope eyepiece portion, actuation means for actuating said endoscope as a function of control signals applied thereto, and first control means attached to said operating body for generating said control signals;
   a parent eyepiece member optically coupled to said endoscope eyepiece and disposed at a position adjacent said operating body, said parent eyepiece member having a mounting end for mounting said parent eyepiece member on said endoscope eyepiece and having a viewing end adjacent said mounting end whereby a first operator of said apparatus can view an image from said viewing end of said primary eyepiece member and can simultaneously operate said first control means attached to said operating body; and
   a remote viewing and control means coupled to said parent eyepiece member for enabling a second operator of said endoscope apparatus to view said image obtained by said image pickup means at a position remote from said operating body and to simultaneously generate endoscope actuating control signals from said position remote from said operating body whereby said first and second operators can each simultaneously view said image and operate said endoscope.

2. An apparatus according to claim 1, in which said image pickup means comprises an objective optical system for obtaining images observable from the distal end of the insertable portion and an image guide fiber having one end portion thereof located at the image forming position of said objective optical system and the other end portion of said image guide fiber disposed in opposing relationship with and optically coupled to said endoscope eyepiece.

3. An apparatus according to claim 1, in which said actuation means comprises a wire for the bending operation which extends through the insertable portion permitting said insertable portion to be bent and a drive motor for operating said wire.

4. An apparatus according to claim 1, in which said actuation means comprises an air feed tube disposed within said insertable portion and an air feed pump for feeding air into said air feed tube.

5. An apparatus according to claim 1, in which said actuation means comprises a water feed tube disposed within said insertable portion and a water feed pump for feeding water into said water feed tube.

6. An apparatus according to claim 1, in which said actuation means comprises a suction tube disposed within said insertable portion and a suction pump for feeding aspirating fluid through said suction tube.

7. An apparatus according to claim 1, further comprising a control valve for controlling said actuation means.

8. An apparatus according to claim 1, wherein said remote viewing and control means comprises a second control means having the same functions as those of said first control means and a transmitting means for transmitting control signals generated by said second control means to said actuation means of said endoscope.

9. An apparatus according to claim 8, in which said transmitting means is detachably mounted on said operating body for transmitting control signals generated by said second control means to said actuation means of said endoscope.

10. An apparatus according to claim 1 wherein said remote viewing and control means has a transmitting means for transmitting control signals generated by said remote viewing and second control means to said actuation means of said endoscope.

11. An apparatus according to claim 10, wherein said transmitting means comprises a signal cable for transmitting control signals generated by said remote viewing and control means, a first electrical contact which is disposed on said parent eyepiece member and connected to said signal cable, and a second electrical contact disposed on said endoscope eyepiece which is detachably connected to said first electrical contact so as to couple to the signal cable and to transmit the control signals to operate said actuation means.

12. A dual viewing and control apparatus for use with an endoscope having an actuation means responsive to control signals applied thereto, said apparatus comprising:
a parent eyepiece member having a mounting end which may be releasably coupled to an eyepiece of an endoscope and a viewing end adjacent said mounting end whereby a first operator of said apparatus can view an image formed by said endoscope from said viewing end of said primary eyepiece member; and
a remote viewing and control means coupled to said parent eyepiece portion for enabling a second operator of said apparatus to view simultaneously with said first operator said image formed by said endoscope at a position remote from said viewing end of said parent eyepiece member and for enabling said second operator to generate endoscope actuating control signals from said remote position.

13. An apparatus according to claim 12 wherein said remote viewing and control means has a transmitting means for transmitting endoscope actuating control signals to said endoscope.

14. An apparatus according to claim 13, wherein said transmitting means comprises a connector which may be detachably mounted to an endoscope and a signal wire having one end attached to said connector and the other end attached to said remote viewing and control means for receiving endoscope actuating control signals.

15. An apparatus according to claim 13, wherein said transmitting means comprises a first electrical contact disposed on said mounting end of said parent eyepiece member and which may be releasably coupled to a second electrical contact of said endoscope and a signal cable having one end attached to said first electrical contact and the other end attached to said remote viewing and control means for receiving and transmitting endoscope actuating control signals.

16. An apparatus according to claim 1 or 12, in which said remote viewing and control means comprises a child eyepiece member disposed at a position remote from the endoscope body, a split optical system for splitting the image obtained on said parent eyepiece member and for guiding said split image by way of an image transmitting optical system to said child eyepiece member and a second control means for generating control signals.

17. An apparatus according to claim 16, in which said split optical system comprises a parent eyepiece lens of the parent eyepiece member, a partially reflecting prism disposed in opposing relationship with the parent eyepiece lens and optically coupled to said parent eyepiece lens, an image forming lens disposed in opposing relationship with said image forming lens and optically coupled to the latter, and a child eyepiece lens of the child eyepiece member in opposing relationship with the other end of said image guide fiber and optically coupled to the latter so that an optical image obtained by the image pickup means of the endoscope can be observed.

18. An apparatus according to claim 16, which further includes a holder formed adjacent to said child eyepiece member and a block which is detachably mounted on said holder and on which said second control means are disposed.

19. An apparatus according to claim 16, in which said second control means is disposed adjacent said child eyepiece member.

20. An apparatus according to claim 1 or 12, in which said remote viewing and control means comprises a remote viewing means and a second control means, said second control means is disposed adjacent to said remote viewing means.

21. An apparatus according to claim 14, in which said second control means is detachably mounted on said remote viewing means.

22. An apparatus according to claim 1 or 12, in which said remote viewing and control means has a switch for generating control signals to the actuation means of the endoscope.

23. A dual viewing and control endoscope apparatus comprising:
an endoscope including an operating body, an insertable portion extending from said operating body, a solid state image pickup means for obtaining an optical image from a distal end of said insertable portion and for converting said image into television signals, and actuation means for actuating said endoscope as a function of control signals applied thereto;
a central control apparatus having a control board and human actuable control means positioned on said control board for generating said endoscope actuating control signals;
a television monitor having a picture image plane for displaying said image of said endoscope and positionable near said control board whereby more than one operator can simultaneously view said image on said picture image plane of said television monitor and can generate control signals from said human actuable control means to said actuation means of said endoscope; and signal transmission means for transmitting control signals generated from said human actuable control means to said actuation means of said endoscope and for further transmitting television signals obtained by said solid state image pickup means of said endoscope and converting them to a picture image on said television monitor.

24. An apparatus according to claim 23, in which said solid state image pickup means comprises an objective optical system for obtaining images observable from the distal end of the insertable portion, and a solid state image pickup element disposed in opposing relationship with said objective optical system and coupled to the latter.

25. A dual viewing and control apparatus for use with an endoscope having an actuation means responsive to control signals applied thereto, said apparatus comprising:

a central control apparatus having a control board and human actuable control means positioned on said control board which are capable of generating endoscope actuating control signals;

a television monitor having a picture image plane for displaying said images obtained from television signals applied thereto and positionable near said control board whereby more than one operator can simultaneously view said image on said picture image plane of said television monitor and can generate endoscope actuating control signals from said human actuable control means; and signal transmission means for transmitting endoscope actuating control signals generated from said human actuable control means and further capable of transmitting television signals applied thereto and converting them to a picture image on said television monitor.

26. An apparatus according to claim 23 or 25, in which said television monitor displays patient's data on its picture image plane.

27. An apparatus according to claim 23 or 25, wherein said television monitor is disposed on said central control apparatus adjacent said human actuable control means.

* * * * *